United States Patent [19]
Jackson

[11] Patent Number: 6,056,753
[45] Date of Patent: May 2, 2000

[54] SET SCREW FOR USE WITH OSTEOSYNTHESIS APPARATUS

[76] Inventor: Roger P. Jackson, 4706 W. 86th St., Prairie Village, Kans. 66207

[21] Appl. No.: 09/114,708

[22] Filed: Jul. 13, 1998

[51] Int. Cl.$^7$ .................................................. A61B 17/56
[52] U.S. Cl. .................................. 606/73; 606/61; 411/5
[58] Field of Search ................................ 606/73, 72, 61, 606/60, 104; 411/5

[56] References Cited

U.S. PATENT DOCUMENTS

| | | |
|---|---|---|
| D. 200,217 | 2/1965 | Curtiss . |
| 791,548 | 6/1905 | Fischer . |
| 2,201,087 | 5/1940 | Hallowell . |
| 2,239,352 | 4/1941 | Cherry . |
| 2,295,314 | 9/1942 | Whitney . |
| 2,532,815 | 12/1950 | Kindsvatter . |
| 2,553,337 | 5/1951 | Shafer . |
| 2,778,265 | 1/1957 | Brown . |
| 2,877,681 | 3/1959 | Brown . |
| 2,927,332 | 3/1960 | Moore . |
| 3,143,029 | 8/1964 | Brown . |
| 3,370,341 | 2/1968 | Allsop . |
| 3,498,174 | 3/1970 | Schuster et al. . |
| 3,584,667 | 6/1971 | Reiland . |
| 3,812,757 | 5/1974 | Reiland . |
| 3,963,322 | 6/1976 | Cryctko . |
| 4,269,246 | 5/1981 | Larson et al. . |
| 4,492,500 | 1/1985 | Ewing . |
| 4,506,917 | 3/1985 | Hansen Arne . |
| 4,641,636 | 2/1987 | Cotrel . |

(List continued on next page.)

FOREIGN PATENT DOCUMENTS

| | | |
|---|---|---|
| 195455 | 9/1986 | European Pat. Off. . |
| 172130 | 2/1987 | European Pat. Off. . |
| 276153 | 7/1988 | European Pat. Off. . |
| 465158 | 1/1992 | European Pat. Off. . |
| 2467312 | 4/1981 | France . |
| 3630863 | 3/1988 | Germany . |
| 373809 | 5/1989 | Germany . |
| 203508 | 9/1923 | United Kingdom . |
| PCT92/03100 | 3/1992 | WIPO . |
| PCT94/10927 | 5/1994 | WIPO . |
| PCT94/10944 | 5/1994 | WIPO . |
| PCT96/06576 | 3/1996 | WIPO . |

OTHER PUBLICATIONS

Two Drawings of Sofamor dated Mar. 10, 1994 and Sep. 20, 1994.
Photocopy of Sofamor Danek GDLH (TM) Posterior Spinal System Locking Screw and label, on sale at least one year prior to the filing of the present application.

*Primary Examiner*—Michael Buiz
*Assistant Examiner*—Julian W. Woo
*Attorney, Agent, or Firm*—Litman, Kraai & Brown, L.L.C.; John C. McMahon

[57] ABSTRACT

An improved set screw with a break off head for use in an osteosynthesis apparatus. The set screw comprising a head or stem preferably having a hexagonal external cross-section, a lower portion having a thread extending around an outer surface thereof and a shank connecting the head to the threaded lower portion. An outer diameter of the shank is equal to a minor diameter of the threaded lower portion, i.e. the outer diameter of the threaded lower portion at the base of the thread. A bore extends into the set screw from an upper surface thereof. The bore has a first bore section and a second bore section wherein the second bore section has a reduced diameter relative to the first bore section and is separated from the first bore section by an internal shoulder. The internal shoulder extends into the bore below an upper end of the thread. The first bore section is sized relative to the shank to result in shearing of the head from the lower portion upon application of a pre-selected torque on the head relative to the lower portion. The stepped down bore configuration also facilitates use of an easy out tool for removing the threaded lower portion, if necessary, from an implant in which it has been secured. The bore may include a plurality of bore sections of increasingly smaller diameter to further facilitate use of an easy out tool.

4 Claims, 2 Drawing Sheets

U.S. PATENT DOCUMENTS

| | | |
|---|---|---|
| 4,763,644 | 8/1988 | Webb . |
| 4,764,068 | 8/1988 | Crispell . |
| 4,790,297 | 12/1988 | Luque . |
| 4,815,453 | 3/1989 | Cotrel . |
| 4,838,264 | 6/1989 | Bremer et al. . |
| 5,005,562 | 4/1991 | Cotrel . |
| 5,067,955 | 11/1991 | Cotrel . |
| 5,073,074 | 12/1991 | Corrigan et al. . |
| 5,129,388 | 7/1992 | Vignaud et al. . |
| 5,147,360 | 9/1992 | Dubousset . |
| 5,154,719 | 10/1992 | Cotrel . |
| 5,261,907 | 11/1993 | Vignaud et al. . |
| 5,261,912 | 11/1993 | Frigg . |
| 5,282,707 | 2/1994 | Palm . |
| 5,312,404 | 5/1994 | Asher et al. . |
| 5,346,493 | 9/1994 | Stahurski et al. . |
| 5,364,400 | 11/1994 | Rego, Jr. et al. . |
| 5,382,248 | 1/1995 | Jacobson et al. . |
| 5,385,583 | 1/1995 | Cotrel . |
| 5,443,509 | 8/1995 | Boucher et al. .......................... 623/16 |
| 5,470,334 | 11/1995 | Ross et al. ................................ 606/72 |
| 5,487,742 | 1/1996 | Cotrel . |
| 5,496,321 | 3/1996 | Puno et al. . |
| 5,499,892 | 3/1996 | Reed . |
| 5,507,747 | 4/1996 | Yuan et al. . |
| 5,562,663 | 10/1996 | Wisnewski et al. . |
| 5,630,817 | 5/1997 | Rokegem et al. . |
| 5,643,260 | 7/1997 | Doherty ..................................... 606/61 |
| 5,653,710 | 8/1997 | Härle . |
| 5,697,929 | 12/1997 | Mellinger . |
| 5,743,914 | 4/1998 | Skiba ........................................ 606/73 |

SET SCREW FOR USE WITH OSTEOSYNTHESIS APPARATUS

BACKGROUND OF THE INVENTION

The present invention relates to improvements in set screws for use with apparatus for correcting orthopedic deformities and, in particular, for use in spinal osteosynthesis.

Surgically implanted spinal osteosynthesis apparatus often include rods which are secured along at least a portion of the spine by a system of hooks, bone screws, including sacral screws and pedicle screws and transverse connectors for the purpose of stabilizing and adjusting spinal alignment. In a very basic apparatus of this type, the hooks and bone screws include a spinal rod bore extending through a ring or body or head of the hook or screw. The screws are screwed into the pedicle portion of the vertebra at desired locations and a spinal rod is then extended through the spinal rod bore in each bone screw.

Where the bone screw has a rod receiving ring and the rod is to be fixed in position in the ring, a set screw is inserted in a threaded bore extending through a wall of the ring, so as to engage the rod, and is then tightened to fix the translational and rotational relationship of the rod within the ring. The rods may then be bent or shaped to maintain an adjacent portion of the spine in a desired configuration, to provide support to the spine and to exert desired corrective or stabilizing forces on the spine.

A slightly more complicated system uses transverse connectors in association with the bone screws to secure the spinal rods. The transverse connectors include an arm and a head. The head has a spinal rod bore extending therethrough. The arm of the connector is inserted through the spinal rod bore in the pedicle screw then the spinal rod may be inserted through the spinal rod bore in the transverse connectors. A threaded bore extends through the head of the connector perpendicular to the axis of the spinal rod bore. Once the rod is inserted through the bore in the transverse connectors the set screws are inserted through the threaded bores and tightened to fix the relative position of the rod within the spinal rod bore, and set screws are inserted in the threaded bores and tightened to fix the position of the transverse connector with respect to the pedicle screws.

The pedicle screws and transverse connectors may be of the closed type as discussed above or of an open end type wherein the head of the screw or connector generally incorporates a U-shaped groove. One type of open end bone screw is shown in the U.S. Patent of Cotrel No. 5,005,562. The device in the Cotrel patent has threaded interior surfaces on the two upright branches that form the rod receiving channel therebetween and which receive a threaded set screw having a rod engaging point and outer ring. The set screw in Cotrel is tightened against the rod by advancing the set screw along the threads. However, this system has limitations. In particular, the ability of the set screw of Cotrel to grip and hold the rod is heavily dependent on the torque applied to the set screw during installation. Unfortunately, the torque is limited because too much torque will cause the branches to spread, thereby allowing the set screw to loosen and the implant to fail. Such failure can also occur when forces are applied to the implant during use, such as at time of muscular stress or during accidents when the back is jolted. To try to overcome this problem associated with the Cotrel device, the implant branches and set screw are increased in size to add strength and/or a retention ring is placed around the outside of the branches to reduce the likelihood of expansion. However, the strengthening adds substantial bulk to an implant and a ring adds bulk and complexity to the implant. In implants, it is important to try to reduce bulk rather than add to it, as it is desirable for the implants to be as low profile as possible.

Rather than have a pair of branches joined only by a set screw or by a set screw and an exterior ring, a cap has been proposed which mates with the branches on opposite sides of the cap to prevent the branches from expanding radially outward upon application of torque to the set screw. The cap also closes off the open end of the bone screw after the rod is placed in the groove in the bone screw. The set screw is then inserted in a threaded bore in the cap and tightened to fix the position of the transverse connector with respect to a respective bone screw. A substantial torque can then be applied to the set screw while held in the surrounding threads of the cap without expanding the bone screw branches.

Various implants such as hooks, pedicle screws and transverse connectors with which the set screw of the present invention is used may be of the closed type, as discussed above, or of an open end type, such as described above, wherein the head of the hook screw or connector generally incorporates a U-shaped groove or slot, an upper end of which may be closed off by a cap after a rod is placed in the open end so as to complete the rod bore. A threaded screw bore for the set screw typically extends through the cap.

The efficacy of the set screw is critical to the overall performance and efficiency of the osteosynthesis apparatus. The set screw must firmly secure the spinal rod or the arm of transverse connectors to prevent rotational or translational movement of the rod or arm after installation. Due to the nature of use of the set screw, it is important that the set screw be relatively small yet constructed to receive sufficiently high torque to firmly set the set screw and hold the rod. The set screw must also be easily manipulated to permit relatively rapid insertion and tightening during surgical procedures. It is also preferable that after insertion, no portion of the set screw extends beyond the threaded bore into which the set screw is inserted. The remaining portion of the set screw should be removable to facilitate disassembling of the osteosynthesis apparatus at any time. It is desirable that the set screw take advantage of physical penetration into the rod so as to improve the strength of the connection to resist axial movement of the rod relative to the set screw over that provided only by abutting friction.

Set screws have been previously developed with breakoff heads or stems which break off after the set screw is inserted through a threaded bore and tightened to a preselected torque. Preferably, no portion of the set screw that remains after the head or stem breaks off extends above or beyond an outer edge of the threaded bore. However, prior art set screws normally have undesirable burrs that are left after the head breaks off that must be removed, thereby making the procedure more difficult or alternatively such burrs may lead to irritation of the patient, if not removed. Often, after installation, a set screw must be removed to reposition a rod or fix a broken apparatus. Prior art set screws have been difficult to remove after the head or stem is broken off. Consequently, it is desirable to have a set screw that can be comparatively easily removed even without a head.

It is also desirable to have a set screw that has an axially aligned tip that penetrates relatively deeply into a rod for preventing movement along or around the rod of an associated implant once tightened, but also includes structure that helps prevent rocking or translational movement of the set screw relative to the point of penetration. Rocking or movement of the screw relative to the location of penetration weakens the grip provided by the tip in the rod and the prevention of such movement substantially strengthens the juncture of the screw and the rod. The set screw tip, such as a point can only penetrate deeply into the rod if sufficient torque can be applied to the set screw to do so. In general greater torque is available due to greater bulk or due to special construction that allows greater strength without adding bulk. The latter is preferred in implants.

It is also desirable to have a set screw that is relatively easy to manufacture to help keep the cost of the screws down.

In general, there is still a need for an improved set screw which is quite strong in size, reliable in securing an osteosynthesis apparatus in place without burrs or high profile, is easily removable and is relatively small yet easily manipulable to facilitate its insertion and removal.

SUMMARY OF THE INVENTION

The present invention comprises an improved set screw for use in an osteosynthesis apparatus primarily for securing and fixing the relative position of a rod within a rod receiving bore of another implant. The set screw has a head or stem preferably having a hexagonal external cross-section, and a lower portion having a thread extending around an outer surface thereof. A shank connects the head to the threaded lower portion. An outer diameter of the shank is equal to a minor diameter of the threaded lower portion, i.e. the outer diameter of the threaded lower portion at the base of the thread. A bore extends into said the set screw from an upper surface thereof. The bore has a first bore section and a second bore section wherein the second bore section has a reduced diameter relative to the first bore section and is separated from the first bore section by an internal shoulder. The internal shoulder extends into the bore below an upper end of the thread. The first bore section is sized relative to the shank to result in shearing of the head from the lower portion upon application of a pre-selected torque on the head relative to the lower portion. The stepped down bore configuration also facilitates use of an easy out tool for removing the threaded lower portion, if necessary, from an implant in which it has been secured. The bore may include a plurality of bore sections of increasingly smaller diameter to further facilitate use of an easy out tool.

OBJECTS AND ADVANTAGES OF THE INVENTION

The objects and advantages of the invention include: providing a set screw for use in an osteosynthesis apparatus for securing a rod or elongate member from rotational and translational movement within a bore of a securement ring or body; providing such a set screw which is relatively small, yet which can be readily manipulated; providing such a set screw which includes a head or stem which breaks off during tightening at a preselected torque after the set screw has been tightened down; to provide such a set screw incorporating means for facilitating removal of the head of the set screw after it has been broken off; to provide such a set screw which incorporates means for facilitating removal of the lower threaded portion of the set screw when desired; and to provide such a set screw which is relatively simple to manufacture and particularly well suited for its intended uses thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
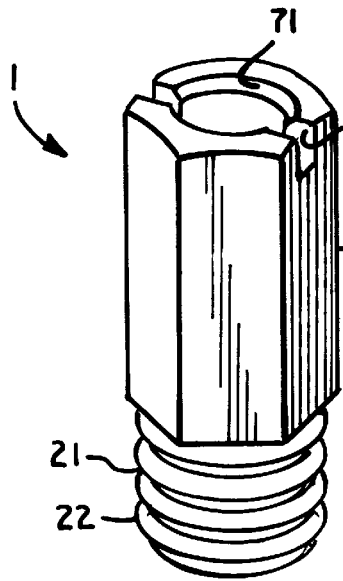
FIG. 1 is a perspective view of a set screw in accordance with the present invention.
Figure 2:
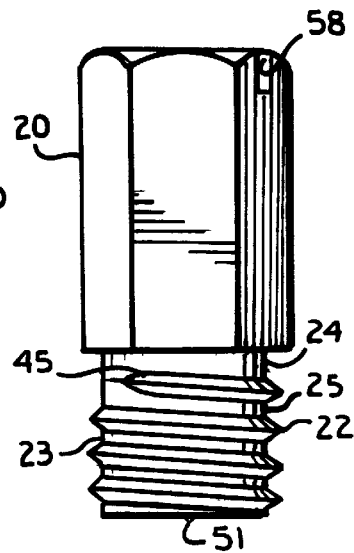
FIG. 2 is a front elevational view of the set screw of the present invention.
Figure 3:
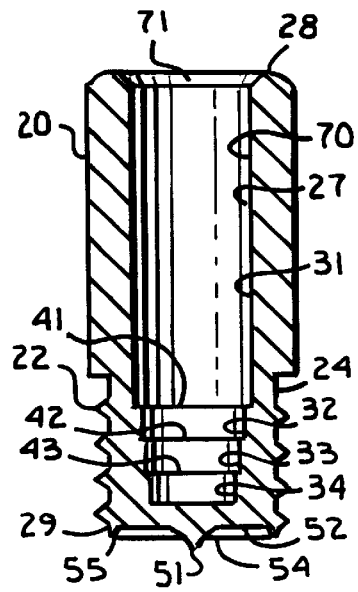
FIG. 3 is a cross-sectional view of the set screw, taken along line 3—3 of FIG. 2 showing a bore extending therein.
Figure 5:
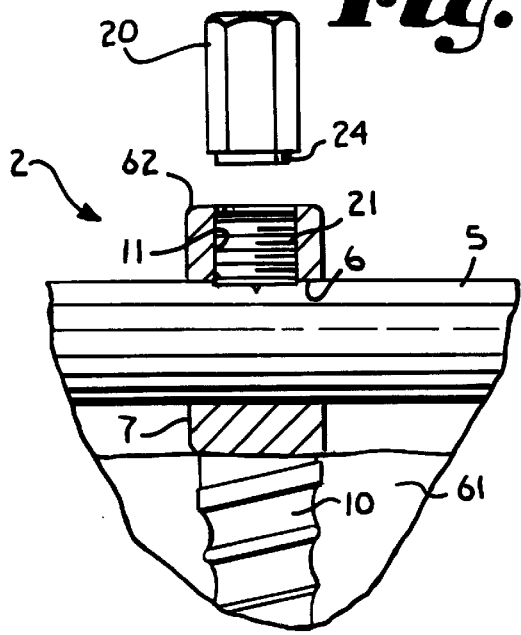
FIG. 5 is a front elevational view on a reduced scale of the set screw showing a lower threaded portion of the set screw engaging a spinal rod secured within a spinal rod bore in a bone screw and showing a head or stem of the set screw after being broken off.
Figure 6:
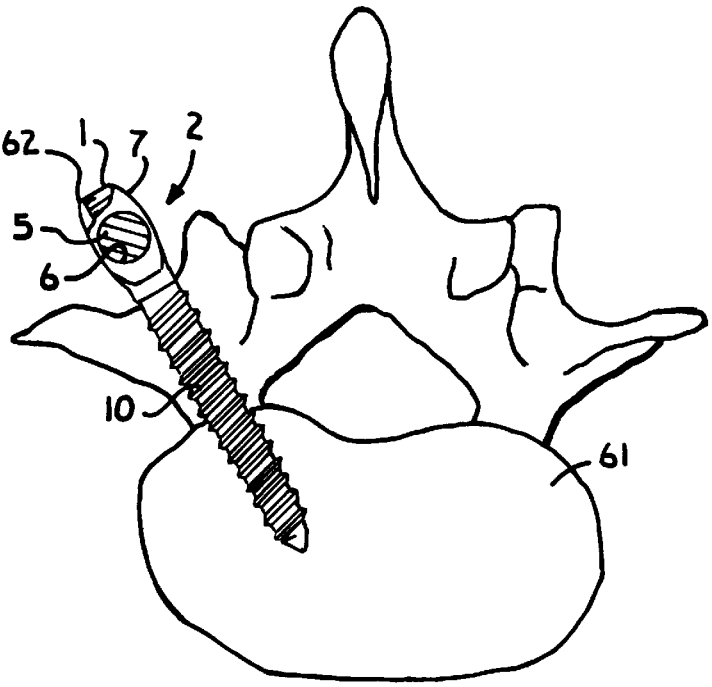
FIG. 6 is a side elevational view on a reduced scale of a bone screw secured within a vertebra and with portions broken away to show a lower threaded portion of the set screw of the present invention secured within the bone screw.

Referring to the drawings in more detail, and in particular FIGS. 1 through 3, the reference numeral 1 generally refers to a set screw for use in osteosynthesis apparatus and in particular for use in spinal osteosynthesis apparatus 2 as shown in FIGS. 5 and 6. Referring to FIGS. 5 and 6, the set screw 1 is adapted for use in securing a rod 5 of the apparatus 2 relative to a rod receiving bore 6 of a head or ring 7, from translational or rotational motion. The ring 7 is of the type formed in the head of a bone screw 10 or the head of a connector or bone hook (not shown) secured to the bone screw 10. In the field of spinal osteosynthesis, the bone screws 10 are often referred to as sacral screws or pedicle screws. The rod 5 may be of the type including spinal rods or the arm or rod portion of a connector. The illustrated rod 5 is round; however, it is foreseen that the rod could be square to help prevent rotation in a similarly shaped bore in the bone screw 10, or have a cross section of almost any shape. A threaded set screw receiving bore 11 extends through the ring 7 perpendicular to the axis of the rod receiving bore 6 and extends radially relative to the ring 7 for the closed hooks, screws and connectors. For open hooks, screws and connectors the angle of point of penetration on the rod may vary with respect to the axis of the rod and to the design for a closing cap thereof.

The set screw 1, as shown in FIGS. 1 through 3, comprises a head or stem 20, of hexagonal external cross-section, a lower portion 21, having a thread 22 extending around an outer circumferential surface 23 thereof and a shank 24 extending between the head 20 and the threaded lower portion 21. The head 20 is relatively elongated to facilitate manipulation of the set screw 1. The shank 24 has an outer diameter which is equal to the diameter of the outer circumferential surface 23 of the lower portion 21, which may also be referred to as the minor diameter of the lower portion 21 which generally comprises the diameter of the lower portion 21 at a base 25 of the thread 22.

As best seen in FIG. 3, a cylindrical stepped down bore 27, is formed in the set screw 1 and extends axially into the set screw 1 from an upper end 28 of the screw 1 toward a lower end 29 thereof. The bore 27 comprises a first bore section 31, a second bore section 32, a third bore section 33 and a fourth bore section 34. The first bore section 31 extends coaxially through the head 20 into the lower portion 21. The first bore section 31 is separated from the second bore section 32 by a first internal shoulder 41 formed in the threaded lower portion 21 and extending radially inward into the bore 27 such that the second bore section 32 is of a reduced or smaller diameter relative to the first bore section 31. The second bore section 32 is separated from the third bore section 33 by a second internal shoulder 42 formed in the threaded lower portion 21 and extending radially inward into the bore 27 such that the third bore section 33 is of a reduced or smaller diameter relative to the second bore section 32. The third bore section 33 is separated from the fourth bore section 34 by a third internal shoulder 43 formed in the threaded lower portion 21 and extending radially inward into the bore 27 such that the fourth bore section 34 is of a reduced or smaller diameter relative to the third bore section 33.

The first internal shoulder 41 preferably extends into the bore 27 below an upper end 45 of the thread 22 and above the point at which the thread 22 completes its first turn. The first or upper bore section 31 is sized to result in shearing of the head 20 from the lower portion 21 at a preselected torque. The first internal shoulder 41 preferably extends into the bore 27 generally just below the upper end 45 thereof to ensure that the head 20 shears off from the lower portion 21 across the shank 24.

As best seen in FIG. 3, a tip, illustrated as a point 51, is formed on a lower surface 52 of the set screw 1 centrally thereof so as to extend outward along a central axis of rotation of the set screw 1. The point 51 forms a point receiving notch, depression, or indentation in the rod 5 against which it is driven. A ring 54 is formed on and extends downward from the lower surface 52 of the set screw 1. The ring 54 extends 360 degrees around the outer periphery of the lower surface 52. A lower edge 55 of the ring 54 is sharpened and adapted to cut into a rod 5 when urged thereagainst. The point 51 preferably extends axially outward and downward further than the ring 54 so as to penetrate deeper into the rod 5 during use.

A drive slot 58 is located at the upper end 28 of the set screw head 20. The slot 58 is a rectangular notch extending downward from the upper end 28 with portions on diagonally opposite sides of the screw 1. The set screw 1 is preferably driven by a hexagonal socket type wrench 60, partially shown in FIGS. 8 and 9. The slot 58 can receive mating parts of the wrench 60; however, the drive slot 58 is adapted to also receive a flat head screwdriver type tool for starting the set screw 1 into the threaded set screw bore 11 in some applications.

In use, the set screw 1 may be inserted in the set screw receiving bore 11 in the ring 7 after the bone screw 10 is inserted into a bone 61 of a patient and after a rod 5 is inserted through the rod receiving bore 6. To secure the rod 5 in position, thereby preventing further rotational or translational movement of the rod 5 with respect to the rod receiving bore 6, the set screw 1 is further driven through the set screw receiving bore 11 until the point 51 and ring 54 engage and bites into the rod 5. Further driving or tightening of the set screw 1 produces torque on the head 20 until a preselected torque is reached which causes the head 20 to shear off along the shank 24 just above the upper end 45 of the thread 22 as shown in FIG. 6 such that the head and substantially all or all of the shank 24 are separated from the lower portion 21. The torque at which the head 20 and shank 24 shear off is selected to ensure sure fixation of the rod 5 within the rod receiving bore 6 without stripping out the set screw receiving bore 11. Penetration of the point 51 and ring 54 into the rod 5 stabilizes the set screw 1 relative to the rod 5, so that the set screw 1 is able to secure the rod 5 and prevent relative movement of the rod 5 with respect to the bone screw 10 even under substantial load.

The set screw 1 and the set screw receiving bore 11 are sized such that the lower portion 21 of set screw 1 and a portion of the shank 24 extend completely within the set screw receiving bore 11 when fully tightened down and such that a lower end of the head 20 does not abut against an upper end 62 of the ring 7 into which it is driven. The set screw 1 is further sized such that the plane across which the head 20 and the shank 24 shear off from the lower portion 21 is slightly below an upper end of the set screw receiving bore 11 in which the lower portion remains or generally flush therewith such that no portion of the set screw lower portion 21 extends beyond the upper end 64 of the ring 7. Further, after the head 20 is sheared off, the resulting upper surface of the set screw lower portion 21 is generally free from burrs or jagged edges.

The set screw 1 may also be pre-loaded into the bone screw 10, or related structure, prior to insertion into the patient. In particular, the set screw 1 may be manually inserted in the threaded set screw receiving bore 11 of a bone screw 20 or a connector before insertion in a patient and rotated a sufficient number of turns such that the set screw 1 is secured in the set screw receiving bore 11, but such that the sharpened ring 54 does not extend substantially into the rod receiving bore 6. The bone screw 10, with the set screw 1 secured thereto, may then be secured into the appropriate bone 61 of a patient. After a rod 5 is inserted through the rod receiving bore 6 of the bone screw 10, the set screw 1 is tightened, as discussed above.

Figure 7:
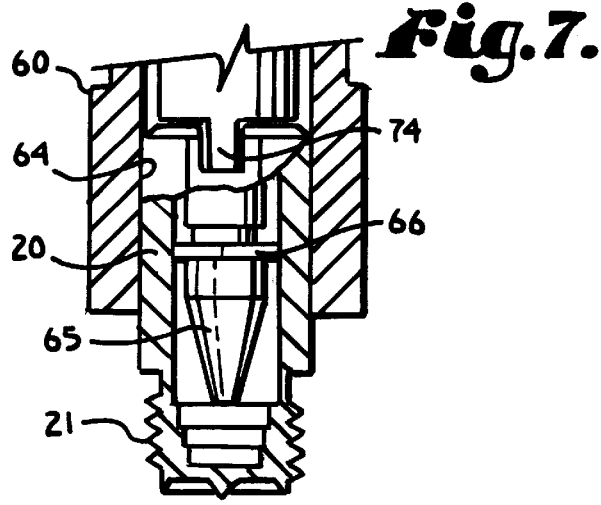
FIG. 7 is a fragmentary front elevational view of the set screw shown secured within a socket wrench with portions broken away to show detail.
Figure 8:
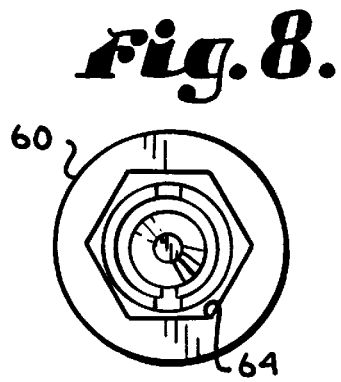
FIG. 8 is a bottom plan view of the socket wrench, as shown in FIG. 7, without a set screw secured therein.

The upper or first bore section 31 of the set screw 1 is adapted to facilitate removal of the set screw head 20 once it is sheared off from the threaded lower portion 21. The set screw is adapted for use with the socket type torque wrench 60, as shown in FIGS. 7 and 8, having a hexagonal socket 64 and a male member or projection 65 extending centrally in the socket. The projection 65 includes a resilient biasing member 66 circumferentially secured thereon. The projection 65 is sized for insertion into at least the upper bore section 31 when the set screw head 20 is positioned in the socket 64. The resilient biasing member 66 biases against an internal wall 70 of the head 20 defining the upper bore section 31 to grip the head 20.

The internal wall 70 has a chamfer 71 at the upper end 28 of the set screw head 20 to facilitate insertion of the projection 65 into the bore 27 in part by facilitating compression of the resilient biasing member 66. The resilient biasing member 66, as shown in FIGS. 7 and 8, generally comprises a split washer type spring, however it is foreseen that the biasing element 66 may be of a wide range of configurations and structures. Further other retention means for releasably securing the set screw 1 to the projection 65 may be utilized including a rubber washer, magnetic coupling means, and various structure producing an interference fit between the projection 65 and the bore 27. Further it is foreseen that means may be provided for gripping of the head 20 by the wrench 60 or related torque inducing tool by engagement of the exterior surface of the head 20.

The projection 65 may include a pair of drive projections or tabs 74 extending laterally from opposite sides of the projection 65 and adapted to mate with the drive slot 58 extending across the upper end 28 of the set screw head 20 to permit an installing surgeon to drive or rotate the set screw 1 by the projection 65.

Figure 9:
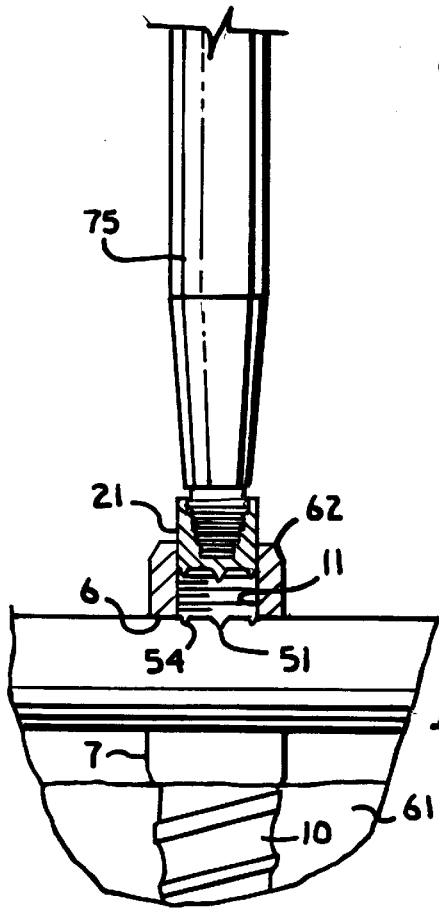
FIG. 9 is a front elevational view similar to FIG. 5 showing use of an easy out type tool to remove a lower threaded portion of the set screw of the present invention from a bone screw.

After the head 20 has been sheared off from the set screw lower threaded portion 21, the second, third and fourth bore sections 32, 33 and 34 are adapted to receive an easy out type tool 75 to permit removal of the set screw lower portion 21 when necessary and as is shown in FIG. 9. The first, second and third internal shoulders 41, 42 and 43 of increasingly reduced diameter facilitate use of the easy out tool 75 which has a downwardly an inwardly tapered end.

The bone screws 10 and related connectors (not shown) discussed above are of a closed end variety in that the ring 7 is of one piece construction. The set screws 1 of the present invention are also adapted for use with bone screws and connectors of the open end variety (not shown). In the open end variety, the ring 7 includes a generally U-shaped groove opening along an upper end of the head or ring 7. A saddle or cap is securable to the head 7 to close off the groove and form the rod receiving bore 6. The set screw receiving bore 11 may be formed in the cap or another part of the head 7.

Figure 4:
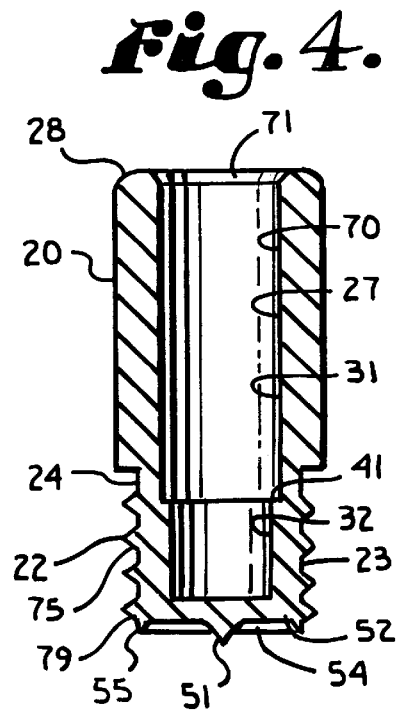
FIG. 4 is a cross-sectional view, similar to FIG. 3 showing an alternative embodiment of the set screw of the present invention.

FIG. 4 discloses an alternative embodiment of the set screw as shown in FIGS. 1 through 3 except that the bore 27 is only divided into first and second bore sections 31 and 32 by first internal shoulder 41 and does not include third and fourth bore sections or second or third internal shoulders. The references numerals in FIG. 4 correspond to the reference numerals of FIGS. 1 through 3 for like parts. It is foreseen any number of bore sections, but at least two, could be utilized with similar results, namely shearing off of the head 20 and shank 24 generally across a plane extending across the shank at the upper end of the thread and providing a starter hole for an easy out tool.

It is noted that while the set screws of the present invention may be used in conjunction with knurled rod, knurling causes the rod to be weakened and fail more easily. Therefore, it is normally preferable to use the set screws of the invention with smooth surface rod. The set screws of the present invention are especially effective in penetrating into and preventing relative motion between the set screw and smooth rod. In addition the set screws of the present invention can be applied with a relatively high torque because the bore in which the set screw is received is closed and completely surrounds the set screw so that it does not spread during torquing and such that the set screws of the present invention can relatively deeply penetrate into rod, especially smooth rod, and hold securely against relative movement while stabilizing the screw with respect to the rod, even when the screw is positioned in the closure cap of an open ended implant. The set screws of the present invention may also be relatively small, for example 5.5 mm. in diameter, and still provide a strong and stable positional stabilization of an associated implant relative to a rod received in the implant.

It is to be understood that while certain forms of the present invention have been illustrated and described herein, it is not to be limited to the specific forms or arrangement of parts described and shown.

What is claimed and desired to be secured by letters patent is as follows:

1. A set screw adapted to be inserted in a threaded bore of a first implant and to set against a second implant for use in a osteosynthesis apparatus comprising:

a) a head shaped for engagement by a torque inducing tool;

b) a lower portion having a thread extending around an outer surface thereof and having a minor diameter at a base of said thread; said thread being sized and shaped to be threadably received in the first implant;

c) a shank extending between said head and said lower threaded portion and having an outer diameter substantially equal to said minor diameter of said lower portion and said head having a diameter greater than said outer diameter of said shank;

d) a bore extending into said set screw from an upper surface thereof; said bore having a first bore section and a second bore section; said second bore section having a reduced diameter relative to said first bore section and separated from said first bore section by a first internal shoulder; said first internal shoulder extending into said bore below an upper end of said thread; said first bore section is sized relative to said shank to result in shearing of said head from said lower portion upon application of a pre-selected torque on said head relative to said lower portion.

2. A set screw for use in a osteosynthesis apparatus comprising:

a) a head shaped for engagement by a torque inducing tool;

b) a lower portion having a thread extending around an outer surface thereof and having a minor diameter at a base of said thread;

c) a shank extending between said head and said lower threaded portion and having an outer diameter equal to said minor diameter of said lower portion;

d) a bore extending into said set screw from an upper surface thereof; said bore having a first bore section and a second bore section; said second bore section having a reduced diameter relative to said first bore section and separated from said first bore section by a first internal shoulder; said first internal shoulder extending into said bore below an upper end of said thread; said first bore section is sized relative to said shank to result in shearing of said head from said lower portion upon application of a pre-selected torque on said head relative to said lower portion; and (e) said first internal shoulder extending into said bore below said upper end of said thread and above a first complete turn of said thread.

3. A set screw for use in a osteosynthesis apparatus comprising:
- a) a head shaped for engagement by a torque inducing tool;
- b) a lower portion having a thread extending around an outer surface thereof and having a minor diameter at a base of said thread;
- c) a shank extending between said head and said lower threaded portion and having an outer diameter equal to said minor diameter of said lower portion;
- d) a bore extending into said set screw from an upper surface thereof; said bore having a first bore section and a second bore section; said second bore section having a reduced diameter relative to said first bore section and separated from said first bore section by a first internal shoulder; said first internal shoulder extending into said bore below an upper end of said thread; said first bore section is sized relative to said shank to result in shearing of said head from said lower portion upon application of a pre-selected torque on said head relative to said lower portion; and
- (e) said bore has a third bore section having a reduced diameter relative to said second bore section and is separated from said second bore section by a second internal shoulder.

4. A set screw for use in a osteosynthesis apparatus comprising:
- a) a head shaped for engagement by a torque inducing tool;
- b) a lower portion having a thread extending around an outer surface thereof and having a minor diameter at a base of said thread;
- c) a shank extending between said head and said lower threaded portion and having an outer diameter equal to said minor diameter of said lower portion;
- d) a bore extending into said set screw from an upper surface thereof; said bore having a first bore section and a second bore section; said second bore section having a reduced diameter relative to said first bore section and separated from said first bore section by a first internal shoulder; said first internal shoulder extending into said bore below an upper end of said thread; said first bore section is sized relative to said shank to result in shearing of said head from said lower portion upon application of a pre-selected torque on said head relative to said lower portion;
- e) said bore has a third bore section having a reduced diameter relative to said second bore section and is separated from said second bore section by a second internal shoulder; and
- f) said bore has a fourth bore section having a reduced diameter relative to said third bore section and is separated from said third bore section by a third internal shoulder.

* * * * *